United States Patent [19]
Davila et al.

[11] Patent Number: 5,562,632
[45] Date of Patent: Oct. 8, 1996

[54] ONE PIECE SELF-ALIGNING, SELF-LUBRICATING CATHETER VALVE

[75] Inventors: Luis A. Davila, Cooper City; Carlo R. De La Mata, North Miami Beach; Stephen J. Querns, Boca Raton, all of Fla.

[73] Assignee: Cordis Corporation, Miami Lakes, Fla.

[21] Appl. No.: 444,217

[22] Filed: May 18, 1995

Related U.S. Application Data

[62] Division of Ser. No. 255,340, Jun. 7, 1994, Pat. No. 5,453,095.

[51] Int. Cl.⁶ ................................................. A61M 5/178
[52] U.S. Cl. ............................................ 604/167; 604/164
[58] Field of Search ................................. 604/167, 256, 604/164, 283, 8; 137/849, 844

[56] References Cited

U.S. PATENT DOCUMENTS

| | | |
|---|---|---|
| 4,424,833 | 1/1984 | Spector et al. . |
| 4,559,043 | 12/1985 | Whitehouse et al. ........... 604/283 |
| 4,568,336 | 2/1986 | Cooper . |
| 4,610,674 | 9/1986 | Suzuki et al. . |
| 4,626,245 | 12/1986 | Weinstein . |
| 4,798,594 | 1/1989 | Hillstead . |
| 4,842,591 | 6/1989 | Luther . |
| 4,895,565 | 1/1990 | Hillstead . |
| 4,909,798 | 3/1990 | Fleischhacker et al. . |
| 4,929,235 | 5/1990 | Merry et al. . |
| 4,932,633 | 6/1990 | Johnson et al. . |
| 4,946,133 | 8/1990 | Johnson et al. . |
| 4,950,257 | 8/1990 | Hibbs et al. . |
| 5,102,395 | 4/1992 | Cheer et al. . |
| 5,114,408 | 5/1992 | Fleischhaker et al. . |
| 5,149,327 | 9/1992 | Oshiyama . |
| 5,167,637 | 12/1992 | Okada et al. . |
| 5,176,652 | 1/1993 | Littrell . |
| 5,203,774 | 4/1993 | Gilson et al. . |
| 5,226,879 | 7/1993 | Enminger et al. . |
| 5,242,413 | 9/1993 | Heiliger . |
| 5,254,097 | 10/1993 | Schock et al. . |
| 5,267,966 | 12/1993 | Paul . |
| 5,304,156 | 4/1994 | Sylvanowicz . |
| 5,324,271 | 6/1994 | Abiuso et al. . |
| 5,338,291 | 8/1994 | Speckman et al. ........... 604/8 |
| 5,350,363 | 9/1994 | Goode et al. . |
| 5,417,665 | 5/1995 | De La Mata et al. ........... 604/164 |

FOREIGN PATENT DOCUMENTS

0344907A2  12/1989  European Pat. Off. .

OTHER PUBLICATIONS

Two sheets of drawings entitled Hemaquet Plus Gasket.

*Primary Examiner*—Sam Rimell
*Attorney, Agent, or Firm*—Gerstman, Ellis & McMillin, Ltd.

[57] ABSTRACT

An elastomeric valve partition is conventionally mounted on a catheter comprising a tubular catheter body. The valve partition defines a central aperture extending inwardly from one of the faces, only partway through the valve partition. The partition also carries a plurality of radial slits extending from the other of the faces only partway through the valve partition and intersecting the central aperture. The central aperture is of a diameter to closely fit a guidewire extending through the valve partition, while the radial slits have a length that is at least double the radius of the central aperture. The slits preferably rotate circumferentially about 5 to 60 degrees as they extend through the valve partition from one face toward the other. A lubricity enhancing additive is present, selected from the group consisting of bismuth oxychloride, polytetrafluoroethylene, titanium dioxide, graphite, polyethylene wax, polyvinylpyrrolidone, and combinations thereof.

6 Claims, 1 Drawing Sheet

ONE PIECE SELF-ALIGNING, SELF-LUBRICATING CATHETER VALVE

This is a division of application Ser. No. 08/255,340, filed Jun. 7, 1994, U.S. Pat. No. 5,453,095.

BACKGROUND OF THE INVENTION

In the allowed Goode et al. U.S. application Ser. No. 08/077,242, filed Jun. 14, 1993 and entitled Enhanced Sheath Valve, a partition valve for a catheter sheath introducer is disclosed having rotating radial slits extending completely through the elastomeric partition valve in a manner similar to Hillstead U.S. Pat. No. 4,895,565. Such slit elastomer medical instrument valves are placed on the proximal end of a catheter sheath introducer, for example, to permit the introduction of a catheter or guidewire into the arterial system of a patient while preventing back bleeding through the proximal end of the catheter sheath introducer, even when a catheter or guidewire is present.

One problem that is found in the present conventional catheter sheath introducers is that after a catheter has been introduced to the arterial system of a patient through the catheter sheath introducer and withdrawn, difficulties may be encountered with the valve in terms of suppression of bleeding if a guidewire is subsequently advanced through the partition valve, since the guidewire is so much smaller than the initial catheter that extended therethrough. This may happen because the catheter may cause some tearing in the slits of the valve. Also, the various flaps of the valve as defined by the slits may not fold together in their proper, original manner. Also, the subsequently applied guidewire may fail to be centered in the valve, which can result in an amount of back bleeding through the valve.

Also, as another technical problem, the elastomers of the Goode et al. application have high elongations, generally being at least 900 percent and more. Such elastomers exhibit a relatively low cross-link density, being tacky and exhibiting an amount of flow resulting from this low cross-link density. Thus, upon storage, it has been found that slits cut out of such elastomers may actually disappear through resealing across the slits, so that they cease to be of optimum use as penetratable seals in a catheter sheath introducer or the like.

By this invention, improvements are provided in which the resealing capability of elastomer valve partitions may be improved, both with respect to the prevention of the resealing of precut slits through the valve partitions. The invention also provides a new valve partition which facilitates the centering of guidewires extending through the partition, while also facilitating the resealing of the valve partition to minimize backbleeding during use. Such a valve partition better tolerates the passage of a larger diameter catheter, followed by a smaller diameter guidewire without exhibiting the previous disadvantage of tearing or substantially leaking blood.

DESCRIPTION OF THE INVENTION

In accordance with this invention, a catheter is provided which comprises a tubular catheter body having a proximal and a distal end. A housing is carried on the proximal end. The housing, in turn carries an elastomeric valve partition having a first face that faces the catheter distal end and a second, opposed face. The valve partition is secured in the housing to prevent flow therethrough.

By this invention, the valve partition defines a central aperture extending inwardly from one of the faces, preferably the second face which faces outwardly (proximally). The central aperture extends only partway through the valve partition. The valve partition also typically carries at least three up to about six radial slits extending from one of the faces only partway through the valve partition toward the other of the faces. The radial slits intersect the central aperture and extend through the face that is spaced from the central aperture.

The central aperture is of a diameter which is intended to closely fit a guidewire extending through the valve partition. The radial slits each have a length that is at least about double the radius of the central aperture. The radial slits also rotate circumferentially by about 5° to 60° as they extend through the valve partition from one face to the other. Specifically, the central aperture may have a diameter of about 0.02 to 0.04 inch, and may have a depth that is from about 100 to 200 percent of the central aperture diameter.

Further in accordance with this invention, the valve partition comprises typically silicone rubber, which preferably may have an elongation to break of at least 900, and typically no more than 1500 percent, as measured by the usual and conventional ASTM D412. The typical prior art slit partition hemostasis valves have a maximum elongation of about 750 percent as measured in similar manner. It has been found that the higher elongations used help to provide improved sealing characteristics over partitions of lower elongation.

Also it is preferred for the elastomeric material to have a tensile strength of at least 11.5 megapascals up to generally a practical maximum of about 15 megapascals as measured by the same ASTM D412. The typical prior art silicone partition valves have a tensile strength of about 10.9 megapascals, significantly below the tensile strength of the preferred elastomer materials used herein.

It is also preferred for the elastomeric materials used herein to have a Shore A durometer of about 20 to 50, although higher durometers may be used if desired.

Specifically, silicone elastomer materials which are preferred for use herein are available from the Dow Corning Corporation of Midland, Mich. under the name Silastic Q7-47-20, 35, or 50 medical grade ETR elastomer. The later two digit numbers refer to the Shore A durometers of the material.

A preferred tear strength of the elastomers used is at least 150 pounds/inch as determined by ASTM D624, Die B.

The use of these materials is taught in the previously cited Goode et al. application.

In accordance with this invention, the valve partition which is preferably made of an elastomer such as the ones described above also contains an effective amount of a lubricity enhancing additive which is a finely divided material selected from the group consisting of bismuth oxychloride, polytetrafluoroethylene, titanium dioxide, graphite, polyethylene wax, polyvinylpyrrolidone, and combinations thereof. The lubricity enhancing additives are typically milled into the uncured elastomer, so as to be substantially uniformly distributed throughout the elastomer material.

Preferably, the graphite is present in a concentration of about 5–15 weight percent. The other specifically mentioned lubricity enhancing additives may be present in a total amount of about 5 to 20 weight percent in the elastomer formulation.

The lubricity enhancing additives provided by this invention not only reduce the friction which is encountered when a catheter or guidewire is advanced through the partition valve and the catheter which carries it, but also, the lubricity enhancing additives serve to prevent the leaflets of elastomer material defined by the slits in the partition valve from sticking to each other with high force. Especially in the situation where the preferred elastomers of high elongation are used as the valve partition, it is possible for the slits which are cut in partitions made of the unmodified elastomer to actually reseal because of the highly tacky characteristic of most silicone elastomers of high elongation. The presence of one of more the additives of this invention can reduce or eliminate this phenomenon, while also reducing frictional forces as a catheter or guidewire is advanced through said valve partition.

It is generally preferred for the additives to be present in a concentration of about 7 to 13 weight percent. By way of specific embodiment, formulations of the above described silicone elastomer have been prepared containing 10 weight percent of, respectively, bismuth oxychloride, PTFE, titanium dioxide, polyethylene wax, and polyvinylpyrrolidone. A similar formulation of such a silicone elastomer has been prepared containing 7.5 weight percent of graphite. The specific Shore A durometers of the silicone rubber silastic ETR Q7-47 formulations tested were 20, 35, and 50. Each of these formulations may respectively contain the above specific amounts of 10 or 7.5 percent of a lubricity enhancing additive as stated, to achieve the desirable results of this invention when formulated into a partition valve and mounted into a catheter sheath introducer.

The radial slits which are formed in the valve partition may be so formed by a cutting process as discussed for example in the Hillstead U.S. Pat. Nos. 4,798,594 and 4,895,565. The central aperture may be premolded into the valve partition. It can be seen that the cutter blades in this invention do not go completely through the disk, since the slits extend only about two-thirds or three-quarters of the way through.

The angle of rotation of the radial slits as they extend through the valve partition may be about 5° to 60°, preferably about 10° to 30°.

The self-aligning, self-lubricating valve partition of this invention provides particular advantage in its reduced frictional characteristics, as well as the improved reclosing characteristics of the valve partition. When a catheter extends through the valve partition, the slits and the aperture readily stretch to accommodate the catheter and allow it to pass through, in part because of the high elongation of the elastomer material. Then, when the catheter is withdrawn, there is an increased tendency for the valve partition to retract back to its original configuration, without physical distortions caused by a high tack encountered between respective slit-defining surfaces so that the partition does not reassume its original configuration. The presence of the lubricity and enhancing additives increases the tendency of the partition of this invention to snap back to its original configuration without being "hung up" prior to achieving the original configuration by adhesion between slit-defining surfaces.

Then, if a guidewire is to be inserted through the valve partition, it tends to be automatically centered by the presence of the central aperture. Even after the system has been stretched to accommodate a catheter of much larger diameter, the valve partition can successfully seal a guidewire which is of much smaller diameter, being spontaneously centered by the presence of the central aperture which is of a diameter that is on the order of the guidewire itself, being typically only slightly larger.

Thus a catheter is provided having a hemostasis valve which exhibits improved characteristics of lubricity and resealing.

DESCRIPTION OF SPECIFIC EMBODIMENTS

Figure 1:
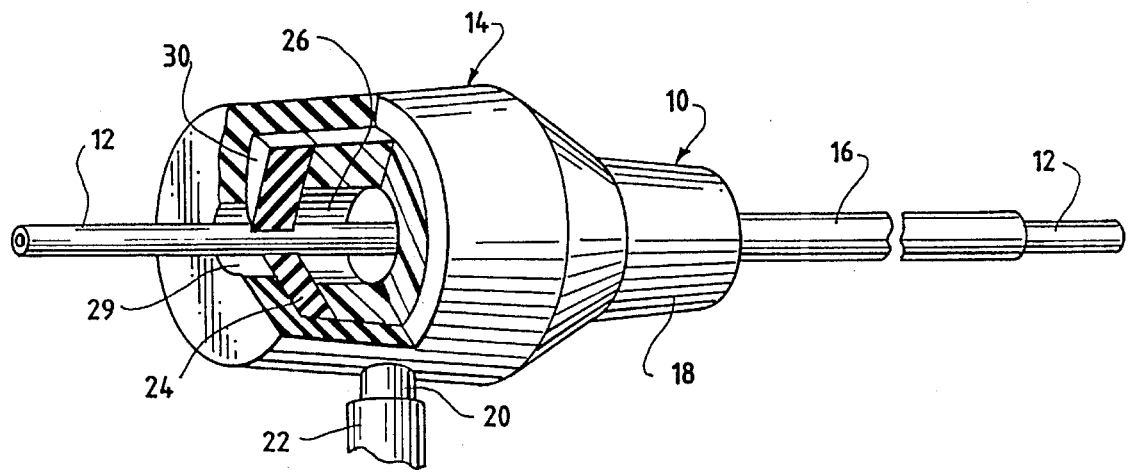
FIG. 1 is a perspective view with a portion broken away of the proximal end of a catheter sheath introducer, modified in accordance with this invention.

Referring to the drawings, FIG. 1 shows a catheter sheath introducer 10, adapted to receive an inner catheter 12 as shown for insertion into the vascular system of a patient. Alternatively, catheter sheath introducer 10 may receive a guidewire of reduced diameter.

As is known, the catheter sheath introducer 10 is used to introduce a catheter or guidewire into a blood vessel, while preventing blood backflow along the outside surface of the catheter or guidewire.

The catheter sheath introducer 10 defines an outer tubular housing 14, and a cannula portion 16 which is relatively short, and is intended to be inserted into the blood vessel to serve as a pathway and a conduit for advancing and retracting catheters and guidewires. Introducer 10 spares injury to the tissue adjacent the access site, and also provides for sealing of the system against blood backleakage caused by arterial pressure.

Outer tubular housing 14 is carried on the proximal end of cannula portion 16, which is attached to tubular protrusion 18 of the housing. Side port 20 may be of conventional design, being adapted for connection with plastic tubing 22, for providing a saline solution for flushing the interior of housing 14 and cannula portion 16.

Housing 14 also carries the elastomeric partition valve 24, which valve 24 is peripherally retained in conventional manner within housing 14. As stated above, partition valve 24 may be made of silicone rubber, but a variety of elastomers may also be used, for example polyurethane elastomers, fluoropolymers, natural rubber latex, and the like.

The specific construction details of housing 14 and the means for retention of partition valve 24 may be the same as is commonly used in the commercially available catheter sheath introducers, and thus do not need to be specifically disclosed.

Catheter 12 is shown to be penetrating through valve partition 24 in sealed relation, in such a manner that the catheter 12 may be advanced or retracted. The interior 26 of housing 14 communicates with the lumen of cannula portion 16 and may be subject to arterial blood pressure through said lumen, but is sealed by valve partition 24.

Figure 2:
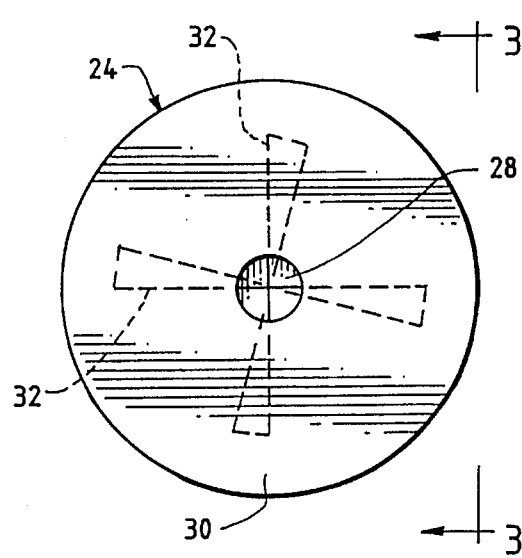
FIG. 2 is an elevational view of the valve partition carried in the catheter sheath introducer of FIG. 1.
Figure 3:
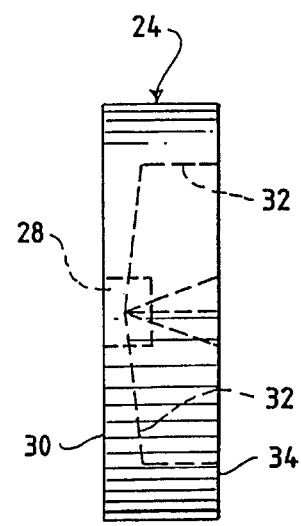
FIG. 3 is an elevational view of the valve partition of FIG. 2, taken along line 3—3 of FIG. 2.

Referring to FIGS. 2 and 3, valve partition 24 can be seen to be a disk of preferably silicone rubber of one of the above described formulations, having an elongation above 900 percent. Specifically, one of the silicone elastomers ETR Q7-47-35, 47-20, or 47-50 may contain either 10 weight percent of bismuth oxychloride or 7.5 weight percent of graphite, uniformly distributed throughout the elastomer in finely divided form. Central aperture 28 is defined in one face 30 of valve partition 24, and is positioned to face away from cannula 16. Central aperture 28 may have a diameter of about 0.02–0.04 inch and a similar depth of about 0.02–0.04 inch. Preferably, the depth is about 100 to 200 percent of the diameter. This diameter dimension assures a fairly close fit with most or all guidewires, so that the guidewires can be centered in the valve partition as they are advanced, for better sealing, even after penetration by a catheter 12 or the like.

Four radial cuts or slits 32 are defined in valve partition 24, beginning at the opposed side 34 of the valve partition and extending inwardly only partway through the thickness of valve partition 24 as shown in FIG. 3. The radial cuts 32 extend more than half way through the valve partition and intersect central aperture 28. Preferably, the thickness of valve partition 24 may be about 0.04–0.08 inch, depending of course in part on the desired dimensions of central aperture 28, which also extends only about half way through the thickness of valve partition 24.

As shown, the radial slits 32 rotate as they extend through the thickness of valve partition 24, the total amount of rotation being about an angle of 15 degrees in this specific embodiment.

Proximal housing aperture 29 may be larger than central aperture 28, to accommodate the largest diameter catheter 12 for which the catheter sheath introducer 10 is designed.

The above is offered for illustrative purposes only, and is not intended to limit the scope of the invention of this application, which is as defined in the claims below.

That which is claimed is:

1. A catheter which comprises a tubular catheter body having a proximal and a distal end, a housing carried on said proximal end, said housing carrying an elastomeric valve partition defining a slit therethrough to permit penetration of an elongated member through the catheter and valve partition, said valve partition comprising an elastomer which contains from about 5 to 20 weight percent of a lubricity enhancing additive selected from the group consisted of bismuth oxychloride, polytetrafluoroethylene, titanium dioxide, graphite, polyethylene wax, polyvinylpyrrolidone and combinations thereof.

2. A catheter of claim 1 in which said valve partition comprises about 5 to 15 weight percent of graphite.

3. The catheter of claim 1 in which said elastomer is silicone rubber having an elongation of at least 900.

4. The catheter of claim 3 in which said additive comprises about 5 to 15 weight percent of graphite.

5. The catheter of claim 2 in which said additive is about 5 to 20 weight percent of bismuth oxychloride.

6. The catheter of claim 5 in which said elastomer is silicone rubber having an elongation of at least 900.

* * * * *